United States Patent [19]

Shore et al.

[11] Patent Number: 5,187,069
[45] Date of Patent: Feb. 16, 1993

[54] ACTIVE SITE LABELLING OF PLASMINOGEN

[75] Inventors: Joseph D. Shore, Grosse Pointe Farms; Paul E. Bock, Hamtramck; Steven T. Olson, Detroit; Duane E. Day, Waterford, all of Mich.

[73] Assignee: Henry Ford Health System, Detroit, Mich.

[21] Appl. No.: 562,702

[22] Filed: Aug. 6, 1990

[51] Int. Cl.$^5$ .......................... C12Q 1/56; C12Q 1/00; G01N 33/86
[52] U.S. Cl. ................................. 435/13; 435/7.71; 436/69; 424/94.64
[58] Field of Search ............... 435/7.71, 13; 436/69; 424/94.64; 930/10; 530/331

[56] References Cited

U.S. PATENT DOCUMENTS

| | | | |
|---|---|---|---|
| 3,884,896 | 5/1975 | Blomback et al. | 530/331 |
| 4,056,519 | 11/1977 | Bobbitt et al. | 530/331 |
| 4,318,904 | 3/1982 | Shaw et al. | 514/18 |
| 4,808,405 | 2/1989 | Smith et al. | 424/94.3 |

OTHER PUBLICATIONS

Paul E. Bock, "Active Site Selective ... Arg-CH$_2$Cl", American Chemical Society, 1988; reprinted from Biochemistry, 1988, 27, 6633.
Biochem. & Biophysical Res. Comm. vol. 57 No. 1, Schick et al. (1974).
Biochemistry vol. 18, No. 6, Nesheim et al. (1979).
Cell Biology: Structure, Biochemistry and Function, Sheeki et al. (1980).
Thrombosis Res. vol. 34, No. 5, Lijnen et al. (1984).
Blood vol. 76, No. 4, Mann et al. (1990).

Primary Examiner—John W. Rollins
Assistant Examiner—Ralph Gitomer
Attorney, Agent, or Firm—Barnes, Kisselle, Raisch, Choate, Whittemore & Hulbert

[57] ABSTRACT

A plasminogen, which has a label incorporated into an active site thereof such that said plasminogen is enzymatically and catalytically inactive upon its conversion to plasmin, and an enzymatically and catalytically inactive plasmin with a label incorporated into an active site thereof.

A method of making a labelled plasminogen which is enzymatically and catalytically inactive upon conversion to plasmin is provided along with an assay method which utilizes a labelled plasminogen.

12 Claims, 3 Drawing Sheets

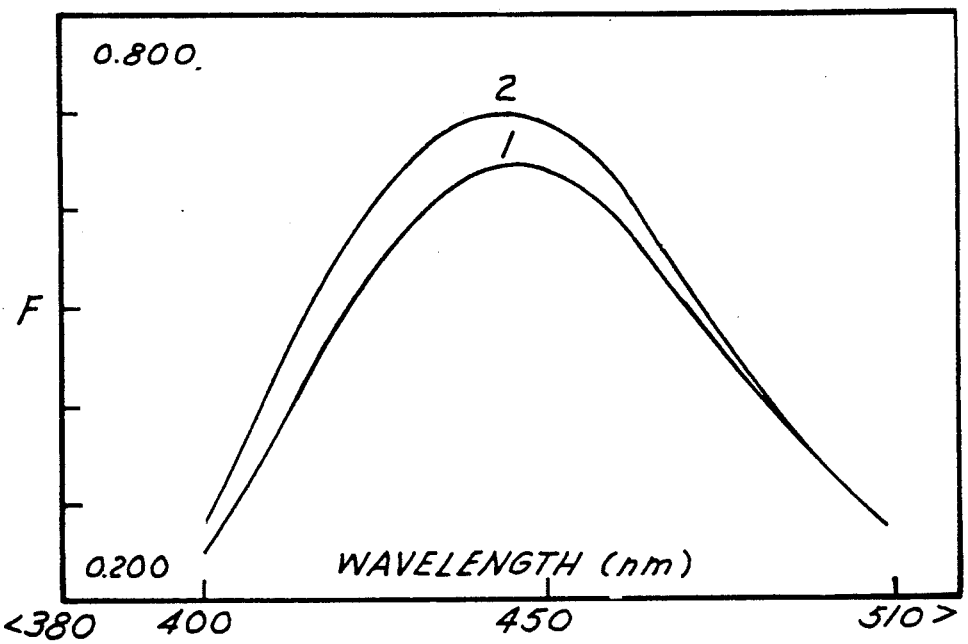
EMISSION SPECTRA OF 0.2 μM ANS-FFR-CK-LABELED GLU-Pgn EXCITED AT 330 nm BEFORE (CURVE 1) AND AFTER (CURVE 2) ACTIVATION WITH UK IN I 0.15 HEPES, pH 7.4, 25°C.
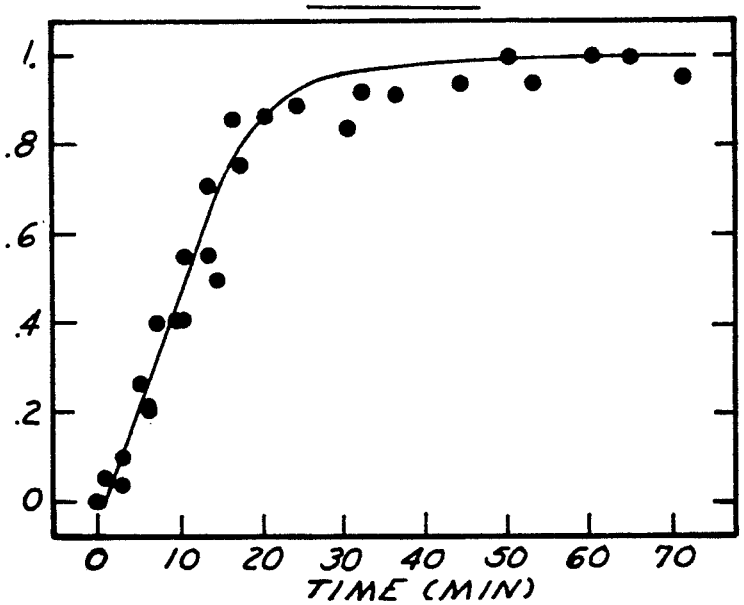
RATE OF ACTIVATION OF 0.2 μM ANS-FFR-CK GLU-Pgn BY 8nM UK OR 20 nM TPA, THE LATTER IN THE PRESENCE OF 50 μg/ml FIBRIN I AND 1 mg/ml GPRP. CONDITIONS AS IN FIG. 2 WITH $\lambda_{em}$ 420nm.

RATE OF ACTIVATION OF 0.2 μM ANS-FFR-CK GLU-Pgn BY 8nM UK OR 20nM TPA, THE LATTER IN THE PRESENCE OF 50 μg/ml FIBRIN I AND 1 mg/ml GPRP. CONDITIONS AS IN FIG.2 WITH $\lambda_{em}$ 420 nm.

ACTIVE SITE LABELLING OF PLASMINOGEN

FIELD OF THE INVENTION

This invention relates to labelled plasminogen which is rendered enzymatically and catalytically inactive upon conversion to plasmin, a method for making same, and a method of use thereof.

BACKGROUND OF THE INVENTION

Various assa methods are currently used for monitoring either urokinase or tissue plasminogen activator, TPA. TPA and urokinase are found in blood and are drugs available for thrombolytic therapy from Genentech, Inc. and Abbott Laboratories, respectively. Both are proteolytic enzymes which convert plasminogen to plasmin, i.e., a serine protease with serine at it active center or site.

Plasmin is responsible for dissolving the fibrin clots or thrombi, formed in various pathologic states such as myocardial infarcts and strokes.

Prior assays for monitoring plasminogen activators such as TPA rely either on reaction of a chromogenic substrate with the plasmin generated in a discontinuous two-stage assay, or a continuous linked assay using a chromogenic substrate with analysis of the parabolic reaction curve of the chromogenic product versus time. The disadvantage of these methods is that the plasmin formed can feed back and cleave either the enzyme urokinase or TPA or the plasminogen substrate resulting in distorted kinetic properties.

Prior methods also include ligand assay using either radioimmunoassay or ELISA, but the disadvantage of this is that it measures the antigenic properties of the plasminogen activator, such as TPA, and thus can not distinguish between active and inactive plasminogen activator, i.e., that which has reacted with inhibitors. Therefore, such assay methods can not distinguish whether the measured TPA is active or inactive because such assay methods monitor total TPA.

Labelling of the serine protease thrombin has been demonstrated by Paul Bock in an article entitled "Active Site Selective Labelling of Serine Proteases with Spectroscopic Probes Using Thioester Peptide Chloromethyl Ketones: Demonstration of Thrombin Labelling Using [(acetylthio)acetyl]-D-Phe-Pro-Arg-CH$_2$Cl". The subject article was originally printed in Biochemistry, 1988, 27, 6633. Although Bock describes a method for attaching fluorescent probes to thrombin, by means of covalent linkages, Bock does not describe or suggest a method for inhibiting the activity of plasminogen, a zymogen, so that the plasmin produced as a result of activating cleavage is catalytically inactive. The structure and function of plasmin and thrombin differ, the reactions which they catalyze differ, and thrombin is not a precursor, or zymogen, as plasminogen is.

Therefore, it is desirable to have an active site labelled plasminogen prepared in a manner which renders it an enzymatically or catalytically inactive enzyme upon conversion to plasmin. That is, a method which would allow direct determination of the action of two chain urokinase and single and two chain TPA, in an assay, without the complications associated with feedback reactions catalyzed by plasmin. This requires a method for making a labelled plasminogen which is enzymatically and catalytically inactive upon conversion to plasmin, and an assay method which utilizes the labelled plasminogen.

SUMMARY OF THE INVENTION

The invention provides a serine protease precursor, plasminogen, with a label at an active site thereof which renders the plasminogen enzymatically and catalytically inactive upon conversion to a serine protease, plasmin. The invention also provides plasmin which is enzymatically and catalytically inactive as a result of a label incorporated into the active site or center thereof. The label provides a detectable change upon the conversion of plasminogen to plasmin. The label may change from a nondetectable state to a detectable state, or the label may exhibit a change in degree of detectability, such as from less to more intense, upon the conversion of plasminogen to plasmin. The label comprises a peptide, derived from a chloromethyl ketone, which is an irreversible inhibitor covalently and specifically bound to the active site of the plasminogen and, which has attached to it a molecule capable of detection. Detectable molecules include chromophores, fluorophores, radioactive molecules, spin label molecules, phosphors and biotin.

In the preferred embodiment, the labelled plasminogen comprises a thioester peptide chloromethyl ketone group and a fluorophore with an acetamide group. Preferably, the peptide comprises D-phenylalanine-L-phenylalanine-L-arginine.

The labelled plasminogen which is enzymatically and catalytically inactive upon conversion to plasmin was developed by a method which includes the specific, covalent incorporation of fluorescence labels into the active site or center of plasminogen which is formed by streptokinase binding. The active plasminogen in the streptokinase-plasminogen (SK-Pgn) complex was first inactivated with a thioester peptide chloromethyl ketone (PCK). The thiol generated by nucleophilic reaction of the incorporated thioester was then covalently labelled with an iodoacetamide derivative of 2,6-ANS, (F-A). The SK was separated from the labelled Pgn by partial dissociation of complex with 0.25M NaSCN, affinity partitioning based reassociation of the labelled plasminogen with an excess of covalently immobilized SK, and elution of the labelled plasminogen, separated from the solution phase SK, from the affinity column.

DETAILED DESCRIPTION OF THE DRAWINGS

FIG. 2 shows an emission spectra of the change in fluorescence of the labelled plasminogen when it is enzymatically converted to plasmin by urokinase.

FIG. 3 shows the change in fluorescence of the labelled plasminogen of the invention upon conversion to plasmin by urokinase.

DETAILED DESCRIPTION OF THE PREFERRED EMBODIMENTS

The invention provides labelled plasminogen from which an enzymatically and catalytically inactive plasmin is generated by the action of plasminogen activating enzymes, a method for making same, and a method of use thereof.

Preferred embodiments of this invention are illustrated by the following examples:

EXAMPLE 1

Figure 1:
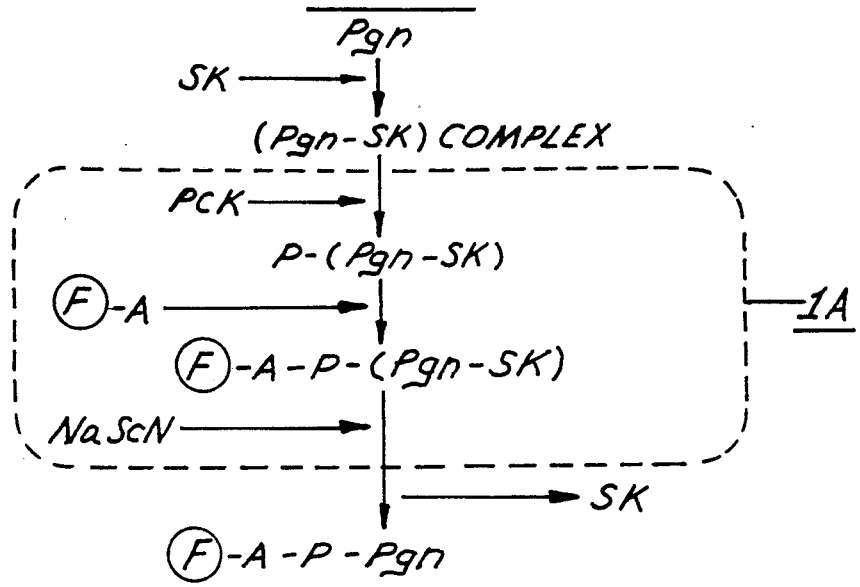
FIG. 1 is a diagram of the formation of a labelled plasminogen (Pgn) which is inactive upon conversion to plasmin.

The overall strategy for creating active site labelled plasminogen relies upon taking advantage of the unique mechanism of action of Streptokinase. Streptokinase (SK) forms a very tight ($K_D=10^{-15}$M) non-covalent complex with plasminogen, which becomes enzymatically active and can cleave other plasminogen molecules. The method includes making the streptokinase-plasminogen (Pgn-SK) complex, reacting the plasminogen with an active site-specific reagent and subsequently with a fluorescent molecule, F-A-PCK-(Pgn-SK), and then dissociating the streptokinase, SK, from it, yielding a plasminogen molecule labelled at what would be the active center after conversion to plasmin, F-A-PCK-(Pgn). The scheme is shown in FIG. 1.

Figure 1A:
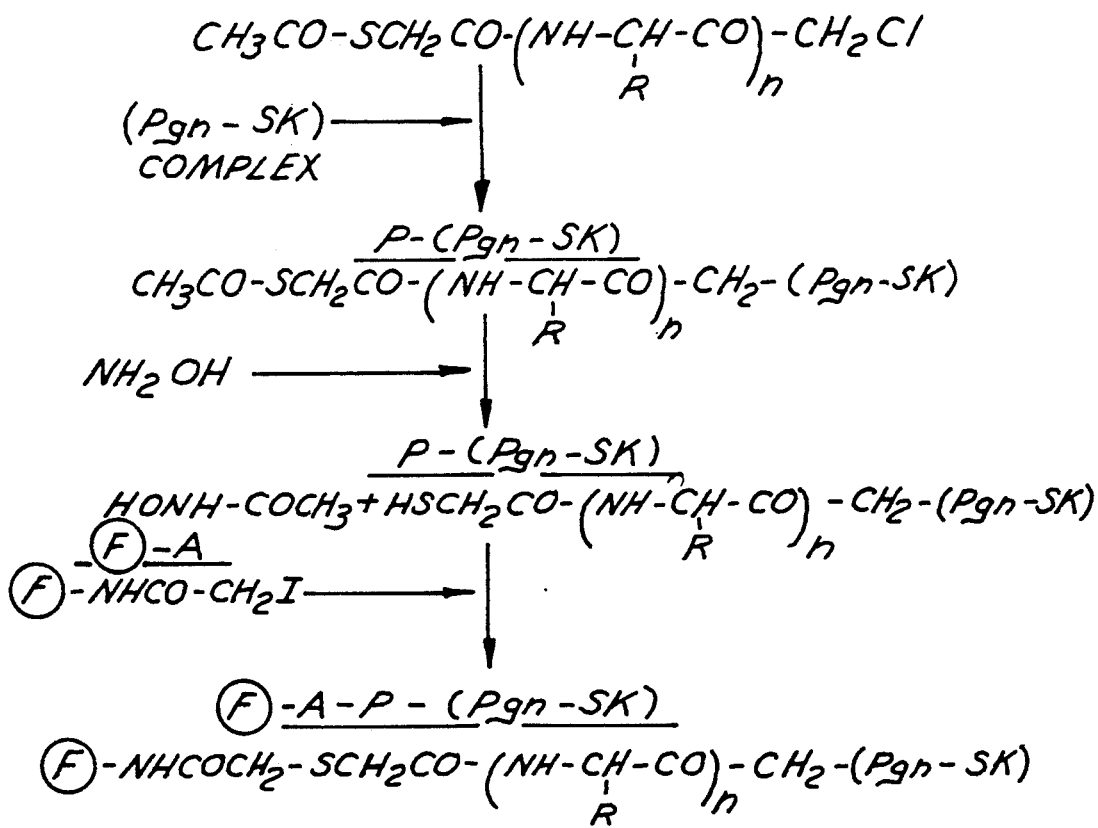
FIG. 1A is a detailed diagram of the encircled portion of FIG. 1, detailing the chemistry of the covalent labelling reactions.

Labelling was performed using a method in which thioester peptide chloromethyl ketones, PCK, were reacted with the histidine residue at the serine protease active center formed in the plasminogen streptokinase complex, followed by generation of a thiol group from the thioester at the ammino terminus of the incorporated PCK with hydroxylamine, and subsequent reaction with a variety of fluorophore-iodacetamides, F-A, available commercially. The scheme for labelling is shown in FIG. 1A. The method of forming the thioester peptide chloromethyl ketone, Nα-[(acetylthio)acetyl]-D-phenylalanine-L-phenylalanine-L-arginine chloromethyl ketone, is known in the art and is as described in Bock cited hereinabove. According to Bock, the method involves addition of the [(acetylthio)acetyl] group of the amino terminus of the commercially available tripeptide chloromethyl ketone, D-Phe-Phe-Arg $CH_1Cl$ by reaction with succinimidyl (acetylthio) acetate, and chlromatogrpahic purification of the product. Bock sugests that other peptide chloromethl ketones may be used, since their rates of reaction with proteolytic enzymes depends on the peptide composition. The label comprised two entities, a peptide bridge or connector (P) and a detectable molecule or marker (F-A). The peptide connector connects a marker to the active site. 5 μM Pgn was complexed with 10 μM SK in the presence of a PCK which was [(acetylthio)acetyl]-D-phenylalanine-L-phenylalanine-L-arginine, chloromethyl ketone, (75 μM ATA-FFRCK), in Hepes buffer, 0.15 μ pH 7.4. After 1.5 hours incubation at 37° C the inactivative complex was then reacted with 150 μM Fluorophore-Iodacetamide, F-A, at 37° C. for 1 hour in the dark, in the presence of 0.1M Hydroxylamine. The solution was then passed over a molecular sieve column to remove free dye. The column was a G-25 sephadex available from Pharmacia, Inc. The solution was then made 0.25M in NaSCN to weaken the Pgn-SK complex and then chromatographed on an immobilized streptokinase column equilibrated in the Hepes buffer at 0.25M NaSCN. The labelled plasminogen was then partitioned on an affinity gel and was subsequently washed with 0.15 μ Hepes to remove free SK and SK-Pgn complex. Labelled Pgn bound to the gel was then step eluted with 3M NaSCN to obtain the final product, F-A-P-Pgn. Using this method, it is possible to link a large variety of labels at the histidine residue of the plasminogen active site or center. The labels were formed using a peptide chloromethyl ketone, [(acetylthio)acetyl]-D-Phenylalanine-L-Phenylalanine-L-A rginine chloromethyl ketone, (ATA FFRCK) with a fluorophore acetamide group attached to the thiol group generated from the thioester group of the inhibitor. The fluorophore acetamide, F-A, was obtained from 2,6-ANS-iodacetamide, (2,6-aniline naphtho sulfuric acidiodacetamide). The label comprised two entities, a peptide bridge or connector (P) and a detectable molecule or marker (F-A). The peptide connector connects a marker to the active site. The labelled Pgn was estimated by PAGE (polyacrylamide gel electrophoresis) to be >95% in the zymogen form. PAGE of the labelled plasminogen, after activation with urokinase or TPA, demonstrated that the fluorescent probe was covalently incorporated into the active site-containing light chain of plasmin.

EXAMPLE 2

Figure 4:
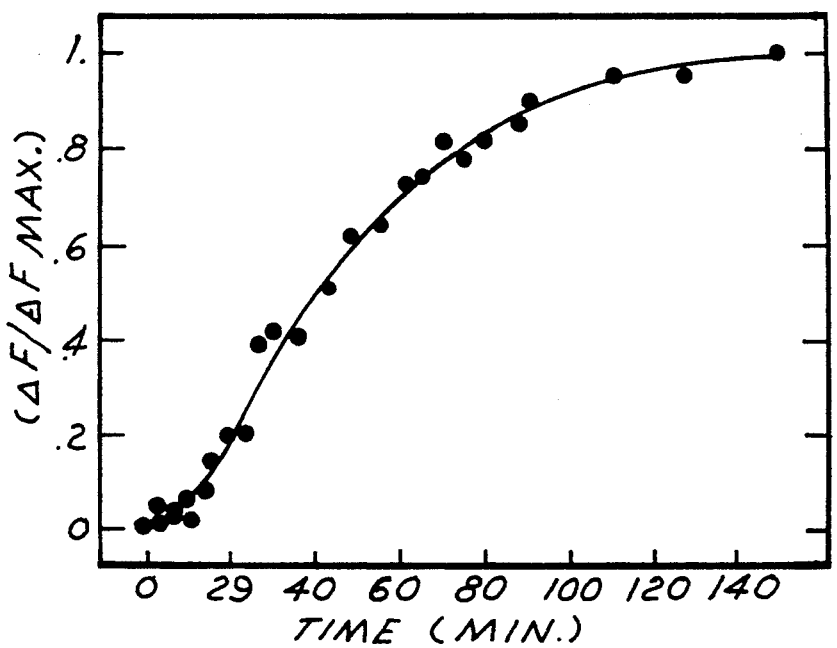
FIG. 4 shows the change in fluorescence of the labelled plasminogen of the invention upon conversion to plasmin by TPA.

The labelled serine protease precursor, plasminogen, was used to monitor directly the action of urokinase and TPA to generate labelled inactive plasmin. The label included the fluorescent probe or marker, 2,6-ANS. In the assay method, the change in fluorescence after proteolytic activation by the components, urokinase and TPA, was monitored as shown in FIGS. 2, 3, and 4.

The fluorescence emission spectra of ANS-FFRCK-labelled plasminogen excited at 330 nm is shown in FIG. 2, which shows a peak at 446 nm. Addition of 8nM urokinase and incubation for 40 minutes resulted in nearly 100% conversion to plasmin as judged by SDS (sodium dodecyl sulfate) gel electrophoresis, and a concomitant 1-2 nm blue shift of the emission spectrum. The fluorescence after proteolytic activation by urokinase showed a 15% enhancement at the peak wavelength of the difference spectrum, 420 nm. Using this fluorescence enhancement signal, it was possible to follow the rate of activation by urokinase or two chain TPA as shown in FIGS. 3 and 4. At various time points aliquots were withdrawn and analyzed by reducing SDS-PAGE (polyacrylamide gel electrophoresis). Fractional cleavage of the labelled plasminogen to heavy and light chains during conversion to plasmin correlated well with the fractional fluorescence enhancements. FIG. 4 shows the activation by TPA in the presence of fibrin I and GPRP (glycyl, prolyl, arginyl, proline) tetrapeptide to inhibit fibrin I polymerization, and demonstrates the accelerating effect of the fibrin. Active site labelled plasminogen prepared by the method described, allows direct study of the action of two-chain urokinase and single and two-chain TPA, without the complications associated with feedback reactions catalyzed by plasmin.

There are numerous uses for the labelled plasminogen species, which include assays for TPA, urokinase, and the streptokinase-plasminogen complex and any other plasminogen activating protease. In binding studies these labelled species could be useful for determining streptokinase concentration by the fluorescence change observed when the labelled plasminogen binds to it, as well as the binding of labelled plasminogen to fibrin. In addition, binding of labelled plasminogen or plasmin to membranes and membrane receptors could be useful in evaluation of biological diversity of cells and in observation of tissues containing plasminogen binding sites by fluorescence microscopy. Many cells, including tumors, contain plasminogen binding sites.

Obviously, many modifications and variations of the present invention are possible in light of the above teachings. Therefore, within the scope of the appended claims, the present invention may be practiced otherwise than as specifically described.

We claim:

1. A plasminogen having a label comprising a peptide chloromethyl ketone attached to a histidine residue which becomes part of an active center of said plasminogen upon cleavage by a plasminogen activator, such that said plasminogen is enyzmatically inactive after proteolytic cleavage by plasminogen activator; said peptide selected from the group consisting essentially of thioester derivatives of arginine-containing peptide chloromethyl ketones and said label comprising a fluorescent probe.

2. A plasminogen according to claim 1, wherein the label comprises said peptide group erived from Nα-[(acetylthio)acetyl]-D-pheylalanine-L-phenylalanine-L-arginine chloromethyl ketone.

3. A process for preparing a labelled plasminogen which is enzymatically inactive upon cleavage by plasminogen activators comprising:
   a) forming a streptokinase-plasminogen complex;
   b) inhibiting the streptokinase-plasminogen complex by attaching a thioester peptide chloromethyl ketone thereto, said peptide selected from the group consisting essentially of thioester derivatives of arginine-containing peptide chloromethyl ketones;
   c) adding a fluorescent probe to the thiol group derived from said thioester peptide chloromethyl ketone by reaction with hydroxylamine thereby forming a labelled complex; and
   d) dissociating and chromatographically separating the streptokinase from the labelled plasminogen thereby forming a fluorescent labelled plasminogen which is enzymatically inactive after proteolytic cleavage by plasminogen activator, and which exhibits a change in fluorescence emission intensity upon cleavage.

4. A process for preparing a labelled plasminogen which is enzymatically inactive upon cleavage by plasminogen activators comprising:
   a) forming a streptokinase-plasminogen complex;
   b) inhibiting the steptokinase-plasminogen complex by attaching a thioester peptide chloromethyl ketone to an active site thereof, said thioester peptide chloromethyl ketone being Nα-[(acetylthio)acetyl]-D-phenylalanine-L-phenylalamine-L-arginine chloromethyl ketone;
   c) adding a fluorescent probe to the thiol group derived from said thioester peptide chloromethyl ketone thereby forming a labelled complex; and
   d) dissociating and chromatographically separating the streptokinase from the labelled plasminogen thereby forming a fluorescent labelled plasminogen which is enzymatically inactive after proteolytic cleavage by plasminogen activator, and which exhibits a change in fluorescence emission intensity upon cleavage.

5. An assay method for plasminogen activators which utilizes a labelled plasminogen which is enzymatically inactive upon cleavage by plasminogen activators comprising:
   a) adding a plasminogen having a label which includes a peptide chloromethyl ketone group and a fluorescent probe to a specimen, said peptide selected from the group consisting essentially of thioester derivatives of arginine-containing peptide chloromethyl ketones; and
   b) monitoring the rate of proteolytic cleavage of said plasminogen by plasminogen activators by observing a change in emission by the fluorescent probe indicating the presence of components which catalyze the cleavage.

6. An assay method according to claim 5, wherein said thioester peptide chloromethyl ketone is Nα-[(acetylthio)acetyl]-D-phenylalanine-L-phenylalanine-L-arginine chloromethyl ketone.

7. A process according to claim 3, wherein steps (a) and (b) are conducted in a relatively neutral solution at a temperature of up to about 37° C.

8. A process according to claim 4, wherein steps (a) and (b) are conducted in a solution at a pH of about 7.4 and at a temperature of up to about 37° C.

9. An assay method according to claim 5 conducted at a relatively neutral pH and at a temperature of up to about 37° C.

10. An assay method for plasminogen activators which utilizes a labelled plasminogen which is enzymatically inactive upon cleavage by plasminogen activators comprising:
   a) adding a plasminogen having a label which includes a peptide chloromethyl ketone group and a fluorescent probe to a specimen, said plasminogen having a label comprising a peptide chloromethyl ketone attached to a histidine residue which becomes part of an active center of said plasminogen upon cleavage by a plasminogen activator, and said peptide selected from the group consisting essentially of thioester derivatives of arginine-containing peptide chloromethyl ketones; and
   b) monitoring the rate of proteolytic cleavage of said plasminogen by plasminogen activators by observing a change in emission by the fluorescent probe indicating the presence of components which catalyze the cleavage.

11. An assay method according ot claim 10, wherein said thioester peptide chloromethyl ketone is Nα-[(acetylthio)acetyl]-D-phenylalnine-L-arginine chloromethyl ketone.

12. An assay method according to claim 10, conducted at a relatively neutral pH and at a temperature of up to about 37° C.

* * * * *